US010738205B2

(12) United States Patent
Dermaut et al.

(10) Patent No.: US 10,738,205 B2
(45) Date of Patent: Aug. 11, 2020

(54) POLYMERIZABLE PHOTOINITIATORS

(71) Applicant: AGFA NV, Mortsel (BE)

(72) Inventors: Wim Dermaut, Mortsel (BE); Peter Goris, Mortsel (BE); Leen Thomassen, Mortsel (BE); Jordy Celis, Mortsel (BE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 16/311,218

(22) PCT Filed: Jun. 15, 2017

(86) PCT No.: PCT/EP2017/064684
§ 371 (c)(1),
(2) Date: Dec. 19, 2018

(87) PCT Pub. No.: WO2017/220425
PCT Pub. Date: Dec. 28, 2017

(65) Prior Publication Data
US 2019/0185689 A1    Jun. 20, 2019

(30) Foreign Application Priority Data

Jun. 23, 2016  (EP) .................................... 16175847

(51) Int. Cl.
| | | |
|---|---|---|
| C09D 11/101 | (2014.01) | |
| C07D 335/16 | (2006.01) | |
| B41M 5/00 | (2006.01) | |
| B41M 7/00 | (2006.01) | |
| C09D 11/38 | (2014.01) | |
| C09D 11/30 | (2014.01) | |
| G03F 7/075 | (2006.01) | |
| G03F 7/031 | (2006.01) | |
| G03F 7/027 | (2006.01) | |

(52) U.S. Cl.
CPC ......... *C09D 11/101* (2013.01); *B41M 5/0023* (2013.01); *B41M 7/0081* (2013.01); *C07D 335/16* (2013.01); *C09D 11/30* (2013.01); *C09D 11/38* (2013.01); *G03F 7/027* (2013.01); *G03F 7/031* (2013.01); *G03F 7/0755* (2013.01)

(58) Field of Classification Search
CPC ..... C09D 11/101; C09D 11/322; C09D 11/38; C09D 11/30; B41J 11/002; B41J 2/01; B41J 2/2107; B41M 5/0023
See application file for complete search history.

(56) References Cited

U.S. PATENT DOCUMENTS

| | | | | |
|---|---|---|---|---|
| 8,985,753 | B2 * | 3/2015 | Loccufier | C08F 2/50 347/100 |
| 2006/0142408 | A1 * | 6/2006 | Liu | C07C 271/12 522/6 |
| 2012/0309861 | A1 * | 12/2012 | Loccufier | C07D 209/86 522/14 |
| 2013/0010039 | A1 * | 1/2013 | Kida | C09D 11/101 347/100 |
| 2013/0210954 | A1 * | 8/2013 | Loccufier | C07D 335/16 522/53 |
| 2014/0285568 | A1 * | 9/2014 | Loccufier | C09D 11/101 347/20 |

FOREIGN PATENT DOCUMENTS

| | | |
|---|---|---|
| EP | 0 029 701 A1 | 6/1981 |
| EP | 2 199 273 A1 | 6/2010 |
| EP | 2 444 429 A1 | 4/2012 |
| EP | 2 684 876 A1 | 1/2014 |
| EP | 2 848 659 A1 | 3/2015 |
| JP | 2004-224993 A | 8/2004 |
| WO | 2008/122812 A2 | 10/2008 |

OTHER PUBLICATIONS

Official Communication issued in International Patent Application No. PCT/EP2017/064684, dated Sep. 14, 2017.

* cited by examiner

*Primary Examiner* — John Zimmermann
(74) *Attorney, Agent, or Firm* — Keating and Bennett, LLP

(57) ABSTRACT

A specific mixture of polymerizable photoinitiators contains a thioxanthone group. A method for manufacturing the mixture of polymerizable photoinitiators uses flow chemistry.

15 Claims, 1 Drawing Sheet

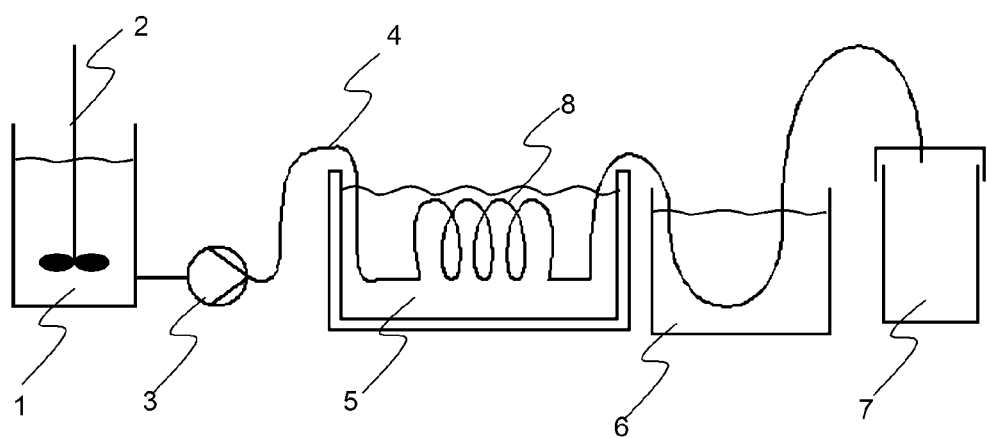

POLYMERIZABLE PHOTOINITIATORS

CROSS REFERENCE TO RELATED APPLICATIONS

This application is a 371 National Stage Application of PCT/EP2017/064684, filed Jun. 15, 2017. This application claims the benefit of European Application No. 16175847.9, filed Jun. 23, 2016, which is incorporated by reference herein in its entirety.

BACKGROUND OF THE INVENTION

1. Field of the Invention

The present invention relates to a mixture of polymerizable photoinitiators, its methods of manufacturing and its use in UV curable compositions and inks.

2. Description of the Related Art

Inkjet printing is replacing conventional printing techniques, such as offset, for printing on packaging. In inkjet printing, tiny drops of ink are projected directly onto an ink-receiver surface without physical contact between the printing device and the ink-receiver. The printing device stores the printing data electronically and controls a print head for ejecting the drops image-wise on an ink-receiver.

Inkjet inks for high resolution, high speed short run digital food packaging printing have to combine low viscosity, low migrating properties after curing and high sensitivity for LED exposure.

Polymeric photoinitiators are known to improve the low migrating properties after curing, but also to increase the viscosity. Hence low viscous, low molecular weight polymerizable photoinitiators have been designed which contain a plurality of polymerizable groups in order to guarantee the low migration properties. It is common knowledge that polymerizable compounds having a single polymerizable group can remain to a certain degree migrateable and extractable, while this probability decreases strongly for a compound having two, three or more polymerizable groups.

Polymerizable thioxanthones, known as preferred photoinitiators for UV LED exposure, have been disclosed for low migration UV curable compositions in EP 2444429 A (AGFA)), EP 2199273 A (AGFA) and JP 2004224993 (NIPPON KAYAKU)).

EP 2684876 A (AGFA) discloses thioxanthone photoinitiators containing a plurality of polymerizable groups, wherein the photoinitiator without isolation may be added directly to a UV curable composition as the batch synthesis was performed in a monomer instead of organic solvent. However scaling-up of this batch synthesis process to a large industrial scale revealed drawbacks. The exothermic reaction has to be carried out at a relative low temperature (e.g. 85° C.) to prevent polymerization requiring long reaction times (e.g. 8 to 10 hours) resulting in a partial degradation of the product. Also an organic solvent, isopropyl acetate, is added as an inhibitor for preventing polymerization. After completion of the reaction, this organic solvent needs to be removed by distillation.

In flow chemistry, a chemical reaction is run in a continuously flowing stream rather than in batch production. In other words, pumps move fluid into a tube, and where tubes join one another, the fluids contact one another. If these fluids are reactive, a reaction takes place. Mixing and heat transfer can be achieved faster and more homogenously than with a batch process. Nevertheless, sometimes a more intense mixing is still required which can be realized by inducing an oscillatory motion, as exemplified in EP 0029701 A (GULF) and WO 2008/122812 (NITECH SOLUTIONS).

EP 0029701 A (GULF) discloses a process and apparatus in which an oscillating motion is superimposed on the linear flow of reactants in order to maintain turbulent flow so that deposit of solids on the walls of tubular continuous flow reactors is avoided.

WO 2008/122812 (NITECH SOLUTIONS) discloses a tubular mixing apparatus and process for applying oscillatory motion to a mixture, wherein the apparatus and process uses a tubular vessel equipped with a plurality of annular baffles configured to initiate and maintain uniform mixing and efficient dispersion of a substance in the tubular vessel.

Another problem, as also mentioned in [0007] in EP 2684876 A (AGFA)), is that in very low viscous UV curable compositions, the type of polymerizable photoinitiator also influences the thermal stability and shelf life upon storage. Fluctuations in viscosity have a large impact on the jetting performance and reliability of the new print heads operating with very low viscous inkjet inks.

Therefore, there is still a need for highly reactive photoinitiators, especially for LED curing, with an improved stability performance in UV curable formulations.

SUMMARY OF THE INVENTION

In order to overcome the problems described above, preferred embodiments of the present invention provide a mixture of photoinitiators as described below.

It was surprisingly found that by performing the synthesis of thioxanthone photoinitiators containing a plurality of polymerizable groups in a specific manner using flow chemistry that improved thermal stability was obtained for the photoinitiator mixture and the inkjet inks made therewith.

It is believed that the improved thermal stability can be allocated to the presence of a polymerizable thioxanthone according to Formula (II) as a side product of the industrial scale flow chemistry synthesis performed at high temperatures for a short time, e.g. 12 minutes at 130° C. In the latter case, also the nitrogen of the amido group reacts with the 2-(2'-vinyloxyethoxy) ethylacrylate resulting in a Formula (II) compound having four acrylate groups. Such a compound is also less migrateable and extractable than polymerizable thioxanthones having one or two acrylate groups which tend to be present as side products in the synthesis of the industrial scale batch process.

Further objects of the invention will become apparent from the description hereinafter.

BRIEF DESCRIPTION OF THE DRAWINGS

FIG. 1 represents a schematic representation of a flow chemistry synthesis set-up to manufacture the mixture of photoinitiators according to the invention. A reaction mixture flows from a supply vessel (1) through a channel (4) in a periodic flow created by a pulsating in-line pump (3) to a heated oil bath (5), and after reaction via a cooling bath (6) to a product vessel (7). The channel (4) may contain multiple curvatures (8).

DETAILED DESCRIPTION OF THE PREFERRED EMBODIMENTS

Definitions

The term VEEA is used for 2-(2'-vinyloxyethoxy) ethylacrylate.

The term "alkyl" means all variants possible for each number of carbon atoms in the alkyl group i.e. methyl, ethyl, for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethyl-propyl and 2-methyl-butyl, etc.

Unless otherwise specified a substituted or unsubstituted alkyl group is preferably a $C_1$ to $C_6$-alkyl group.

Unless otherwise specified a substituted or unsubstituted alkenyl group is preferably a $C_1$ to $C_6$-alkenyl group.

Unless otherwise specified a substituted or unsubstituted alkynyl group is preferably a $C_1$ to $C_6$-alkynyl group.

Unless otherwise specified a substituted or unsubstituted aralkyl group is preferably a phenyl or naphthyl group including one, two, three or more $C_1$ to $C_6$-alkyl groups.

Unless otherwise specified a substituted or unsubstituted alkaryl group is preferably a $C_7$ to $C_{20}$-alkyl group including a phenyl group or naphthyl group.

Unless otherwise specified a substituted or unsubstituted aryl group is preferably a phenyl group or naphthyl group.

Unless otherwise specified a substituted or unsubstituted heteroaryl group is preferably a five- or six-membered ring substituted by one, two or three oxygen atoms, nitrogen atoms, sulphur atoms, selenium atoms or combinations thereof.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms.

Unless otherwise specified a substituted alkyl group, a substituted alkenyl group, a substituted alkynyl group, a substituted aralkyl group, a substituted alkaryl group, a substituted aryl and a substituted heteroaryl group are preferably substituted by one or more constituents selected from the group consisting of methyl, ethyl, n-propyl, isopropyl, n-butyl, isobutyl and tertiary-butyl, ester, amide, ether, thio-ether, ketone, aldehyde, sulfoxide, sulfone, sulfonate ester, sulphonamide, —Cl, —Br, —I, —OH, —SH, —CN and —$NO_2$.

Photoinitiator Mixtures

A mixture of photoinitiators according to the invention contains the polymerizable photoinitiators according to Formula (I) and (II):

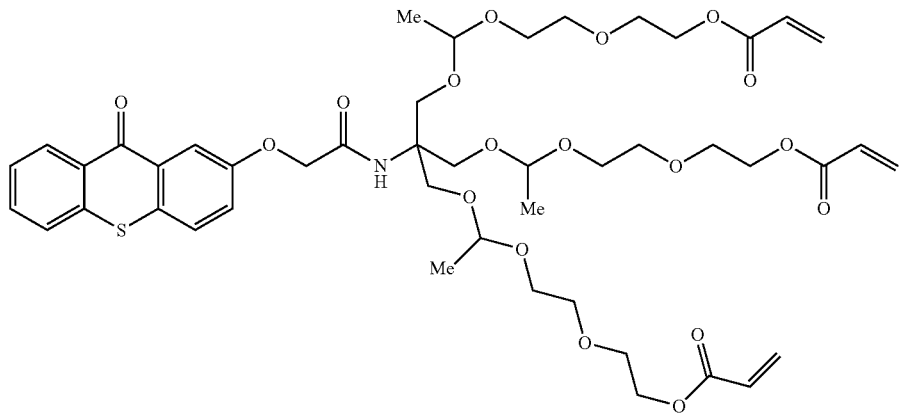

Formula (I)

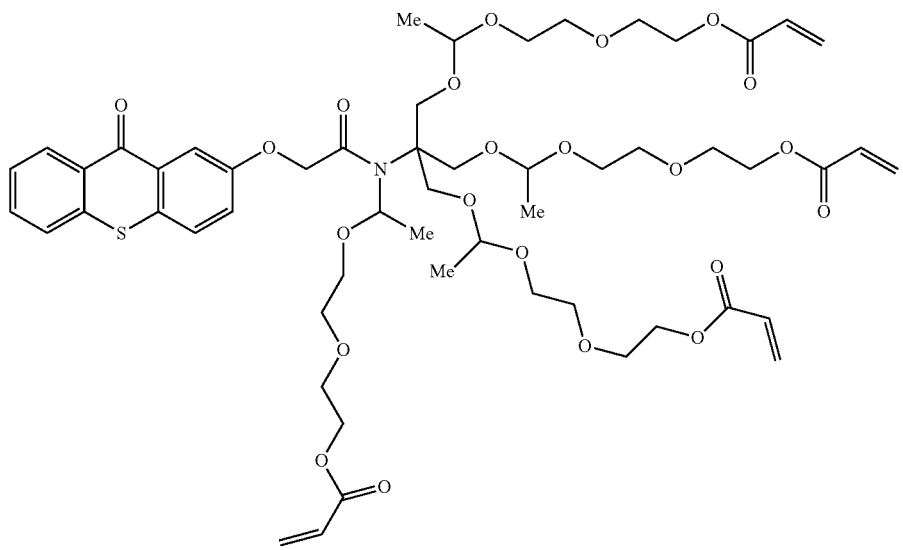

and Formula (II)

In a particularly preferred embodiment of the mixture of photoinitiators, the polymerizable photoinitiator according to Formula (II) is present in an amount of 0.1 wt % to 20.0 wt %, more preferably no more than 10.0 wt % based on the total weight of polymerizable photoinitiators according to Formula (I) and (II). The polymerizable photoinitiator according to Formula (I) is preferably present in amount of 75.0 wt %, more preferably 80.0 to 99.9 wt % based on the total weight of polymerizable photoinitiators.

If the polymerizable photoinitiator according to Formula (I) is present in an amount of at least 75 wt %, then no monoacrylated photoinitiator was observed to be present.

In an even more preferred embodiment of the mixture of photoinitiators, the mixture of photoinitiators consists of the polymerizable photoinitiators according to Formula (I) and (II).

Manufacturing Methods

A method of manufacturing a mixture of photoinitiators according to the invention includes the steps of: flowing a reaction mixture containing a photoinitiator according to Formula (III):

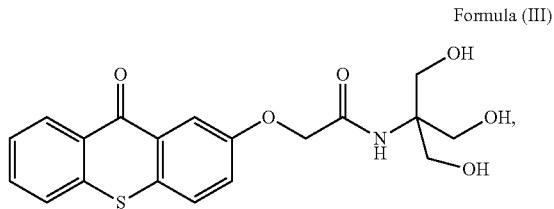 [SMILES: O=C(COc1ccc2sc3ccccc3c(=O)c2c1)NC(CO)(CO)CO]

Formula (III)

solid catalyst particles having an average particle size between 10 μm and 500 μm, and 2-(2'-vinyloxyethoxy) ethylacrylate (VEEA) through a channel (4) in a periodic flow at frequencies up to 100 Hz; heating the reaction mixture to a temperature above 90° C. so that a polymerizable photoinitiator according to Formula (II) is formed:

cooling the reaction mixture to a temperature below 30° C.; and removing solid catalyst particles.

In a first embodiment, the reaction mixture containing a photoinitiator according to Formula (III), solid catalyst particles having an average particle size between 10 μm and 500 μm, and VEEA is obtained by two or more channels (4) joining one another prior to being heated, in e.g. an oil bath (5).

In a second embodiment, the reaction mixture is first mixed in a supply vessel (1) after which it flows through a channel (4) having an inlet attached to the supply vessel (1) and an outlet attached to a product vessel (7).

A periodic flow means that an oscillation is superimposed over a steady linear flow, preferably by means of a pulsation device ("pulsator"). The periodic flow is defined by its frequency (number of cycles per unit of time) and its amplitude (magnitude of the deviation in flow velocity).

If the amplitude of the oscillation is larger than the linear flow component, the direction of flow will be reversed during a certain period of time of the cycle. This is referred to as oscillatory flow. If the amplitude of the oscillation is smaller than the linear flow component, the net flow velocity remains positive at all times. This is referred to as pulsatile flow. Oscillatory flow is sometimes also referred to as reverse pulsatile flow. A periodic flow wherein the net flow is equal to the pulsation amplitude is known as a start-and-stop flow. In a preferred embodiment, the periodic flow is a pulsatile flow or a start-and-stop flow, preferably a pulsatile flow.

The oscillatory motion may occur at frequencies up to 100 Hz, more preferably up to 10 Hz. And most preferably up to 8 Hz. At higher frequencies, the removal of polymerization deposit on the inner wall of the channel becomes less efficient. In a particularly preferred embodiment, the periodic flow is performed at a frequency between 2 and 5 Hz. Preferably also a small counter pressure is provided at the end of the channel to prevent cavitation in the channel.

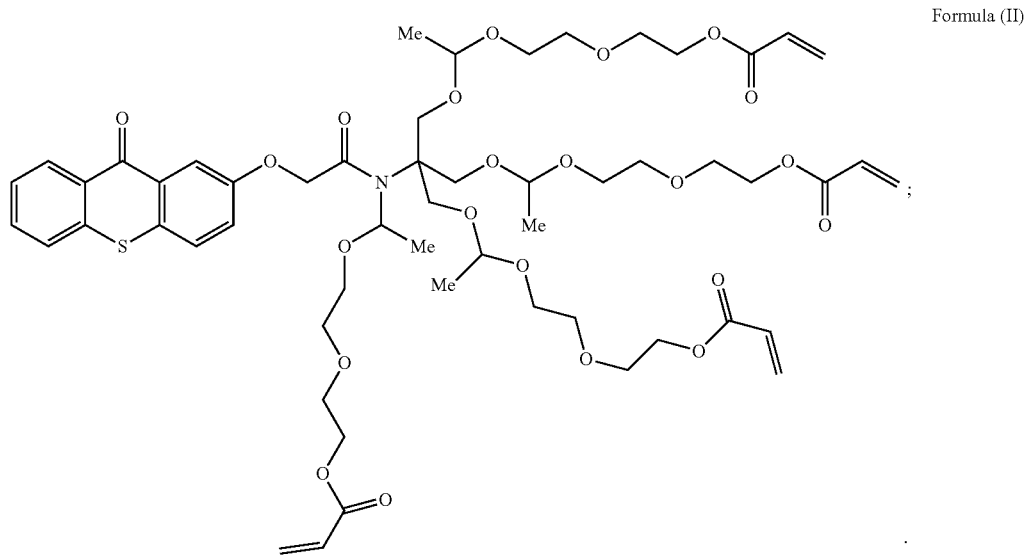 [SMILES: C=CC(=O)OCCOCCOC(C)OCC(COC(C)OCCOCCOC(=O)C=C)(COC(C)OCCOCCOC(=O)C=C)N(C(=O)COc1ccc2sc3ccccc3c(=O)c2c1)C(C)OCCOCCOC(=O)C=C]

Formula (II)

Unlike with batch synthesis, an easy scaling-up may be performed simply by using a plurality of identical channels (4). For example in the second embodiment here above, a second channel having an inlet attached to the supply vessel (1) and an outlet attached to a product vessel (7) may be provided for flowing the reaction mixture simultaneously through two channels in a periodic flow, preferably a pulsatile flow or a start-and-stop flow.

A periodic flow of the reaction mixture was found to be the most appropriate manner for thorough mixing of the reaction mixture in the channel (4) as it was observed that otherwise polymerized material was deposited on the inner wall of the channel. This polymerization is often caused by reaction of the vinylether group in VEEA with acid contaminants present in e.g. the solid particle catalyst, such as sulfonic acid or sulfuric acid.

Multiple ways exist for generating a periodic flow in a channel. For example, WO 2015/056156 A (UNIVERSITY DO PORTO) discloses an improved apparatus for mixing intensification in multiphase systems based on oscillatory flow mixing (OFM) and comprising a novel oscillatory flow reactor (OFR) provided with Smooth Periodic Constrictions (SPCs). WO 2008/122812 (NITECH SOLUTIONS) discloses a tubular mixing apparatus and process for applying oscillatory motion to a mixture using a tubular vessel equipped with a plurality of annular baffles.

However it was observed that including physical constrictions (SPCs) and obstacles, such as also static mixers in the channel (4) of the flow chemistry apparatus resulted after a while in clogging of the channel. An example of a static mixer is given by EP 0071454 A (KENICS). For industrial manufacturing, it is desired that such clogging is prevented. It was found that the best way to generate a periodic flow is to use a so-called pulsator or pulsating mechanism as exemplified in EP 0029701 A (GULF). The pulsator can, for example, consist of a rigid chamber containing a reciprocating piston or diaphragm, which may be driven by positive mechanical driving means.

In a preferred embodiment, the pulsation is provided by a pulsating in-line pump (3). These pumps are well-known to one skilled in the art. Commercially available examples include ProMinent® solenoid pumps.

The pulsator or pulsating in-line pump (3) may be mounted after heating or cooling of the reaction mixture in the channel (4) took place, but preferably it is mounted in the channel (4) before the reaction mixture is heated.

Further improved mixing may be obtained by including multiple curvatures (8) of the channel (4) causing changes in flow velocity of the reaction mixture (higher velocity at outer curvature compared to inner curvature in the channel). The presence of multiple curvatures also allows minimizing the size of the heating means, e.g. the oil bath (5), representing an economical advantage.

The channel is preferably a helical tube with a plurality of curvatures or turns. Preferably, the channel has 2 to 10,000 turns, more preferably 10 to 500 turns. The helical tube preferably has a circular radial cross-section, making it a circular helix tube.

The cross-section of the channel may have any desired shape such as rectangular, square, elliptical and circular, but is preferably elliptical or circular and most preferably circular. A circular cross-section provides for optimal mixing, especially in combination with a plurality of curvatures (preferably Dean Number less than 3000).

The channel is preferably opaque. It is common knowledge for a person skilled in the art of polymerizable photoinitiators that the manufacturing thereof is performed as much as possible under light conditions in which actinic radiation has been substantially excluded.

The polymerizable photoinitiator according to Formula (I) is synthesized according to the following reaction scheme:

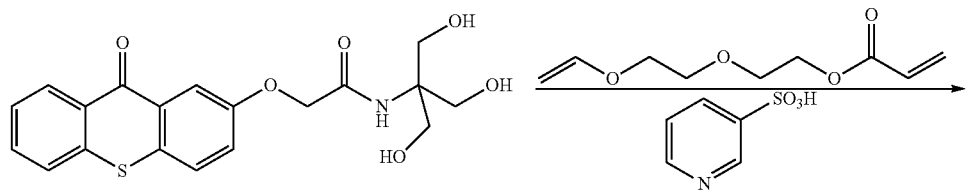

Formula (III)

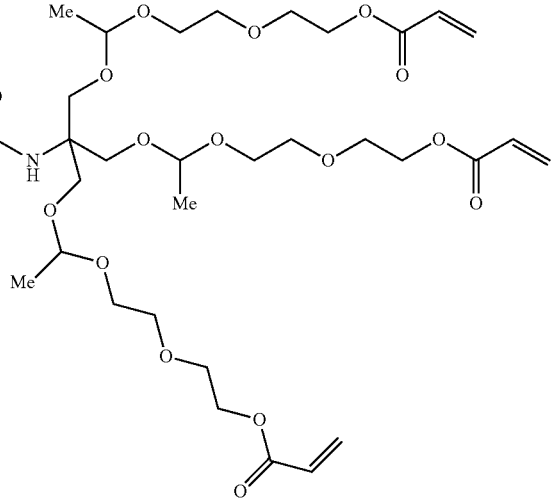

Formula (I)

The photoinitiator according to Formula (III) has three hydroxyl groups, which can all react with VEEA on the surface of the pyridine sulfonic acid particles. For preventing polymerization in a batch synthesis, the reaction temperature is usually kept around 80 to 85° C. and isopropyl acetate is usually added as a thermal buffer for moderating temperature increases. In industrial scale synthesis also mono- and diacrylated side products of the triacrylated polymerizable photoinitiator according to Formula (I) may be observed in the end-product, due to the fact that only one respectively two of the hydroxyl groups in the photoinitiator according to Formula (III) have reacted with VEEA.

Using a flow chemistry process at temperatures above 90° C., the presence of the monoacrylated side product is effectively prevented in the end product. Furthermore, the polymerizable photoinitiator according to Formula (I) often also contains no or only minor amounts of the diacrylated side product. Instead it was observed that a polymerizable photoinitiator according to Formula (II) is present in small amounts due to the fact that at these higher temperatures also the nitrogen in the amido function reacts with VEEA forming the tetra-acrylated photoinitiator according to Formula (II).

Furthermore, the synthesis by a flow chemistry process is simplified as it can be performed in the absence of isopropyl acetate, which has the advantage that this organic solvent must not to be removed by distillation at the end of the synthesis. Removal of this organic solvent is also required for use of the polymerizable photoinitiator mixture in a UV curable inkjet ink as it has a detrimental effect on latency in the inkjet printing process. After filtration of the solid catalyst particles, which may be re-used in a next synthesis, the end product preferably consists essentially of the polymerizable photoinitiators according to Formula (I) and (II) dissolved in VEEA. Although VEEA may be removed, it is advantageous to add this liquid end product directly to UV curable compositions and inks. Extra costs and possible problems for dissolving the polymerizable photoinitiators are thereby avoided. Problems of dissolving crystallized polymerizable photoinitiators prepared in an organic solvent are well-known to those skilled in the art.

The time period for heating the reaction mixture above 90° C. can be easily determined by the person skilled in the art of flow chemistry based on the analysis of the end product, e.g. the concentration of the polymerizable photoinitiator according to Formula (II). The heating period can be controlled by the length of the heated channel (4) and/or the flow rate, the latter usually expressed in L/hour.

In a preferred embodiment of the manufacturing method, the reaction mixture is heated to a temperature between 100° C. and 150° C., more preferably between 120 and 140° C. for a period of less than 20 minutes, more preferably less than 15 minutes. At such conditions, high productivity is obtained without excessive formation of degradation products, such as acetaldehyde. The polymerizable photoinitiator according to Formula (II) is then also present in an amount of 0.1 wt % to 20.0 wt % based on the total weight of polymerizable photoinitiators according to Formula (I) and (II).

Solid Catalyst Particles

The solid catalyst particles have an average particle size between 10 μm and 500 μm as measured by laser diffraction on the dry powder. A preferred commercially available apparatus for measuring the average particle size is a Coulter™ LS13320 Tornado equipped with a dry powder module.

The smaller the solid catalyst particle, the larger the specific surface and the higher the reactivity of the catalyst particles. However, below 10 μm the reactivity becomes too high and not all catalyst particles can be effectively removed by filtration form the end product. Above 500 μm clogging of the channel (4) is often observed.

The solid catalyst particles are preferably made of a zwitterionic catalyst comprising at least one basic nitrogen containing structural fragment and at least one sulfonic acid in its structure, with the proviso that the basic nitrogen on sulfonic acid molar ratio is 1 over 1.

The zwitterionic catalyst is preferably selected from the group consisting of sulfonated pyridines, quinolines, isoquinolines, imidazoles, benzimidazoles and anilines.

In a preferred embodiment, the zwitterionic catalyst is represented by Formula (SCP):

Formula (SCP)

wherein, $L_1$ represents a divalent linking group selected from the group consisting of a substituted or unsubstituted alkylene group, alkenylene group, alkynylene group and arylene group; n represents 0 or 1; and Q represents the necessary atoms to form a substituted or unsubstituted pyridine ring. The divalent linking group $L_1$ preferably contains 1 to 20 carbon atoms.

In a preferred embodiment, the catalyst according to the present invention is selected from the group consisting of 2-pyridine sulfonic acid, 3-pyridine sulfonic acid and 4-pyridine sulfonic acid.

In a particularly preferred embodiment, the solid catalyst particles consist substantially of 3-pyridine-sulfonic acid.

Preferred catalysts used in the process according to the present invention are shown in Table 1, without being limited thereto.

TABLE 1

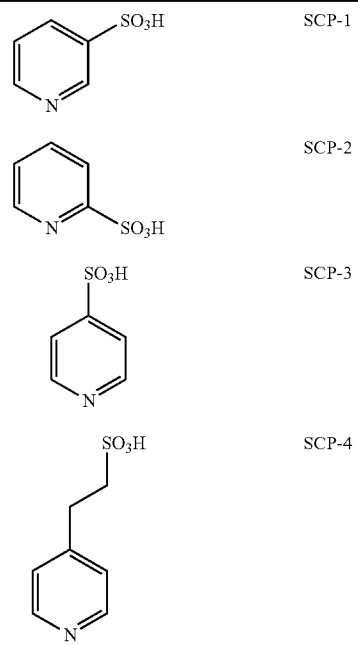

TABLE 1-continued

| | |
|---|---|
| 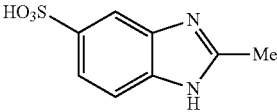 [SMILES: Cc1nc2cc(S(=O)(=O)O)ccc2[nH]1] | SCP-5 |
| 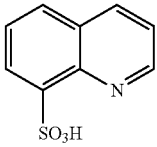 | SCP-6 |
| 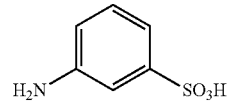 | SCP-7 |
| 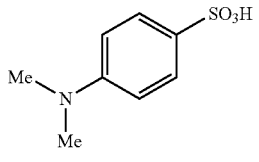 | SCP-8 |
| 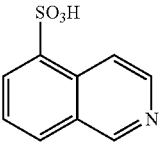 | SCP-9 |
| 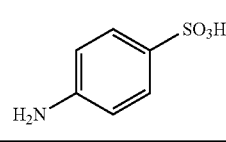 | SCP-10 |

UV Curable Compositions and Inks

A preferred UV curable composition contains the mixture of photoinitiators according to Formula (I) and (II) and further 2-(2'-vinyloxyethoxy) ethylacrylate as a monomer.

In a more preferred embodiment, the UV curable composition further contains a colorant. In such a case the UV curable composition is usually called a UV curable ink.

The UV curable composition may be a colourless UV curable inkjet ink, such as a varnish or a primer, but preferably it is a coloured UV curable inkjet ink, preferably having a colour selected from white, black, cyan, magenta, yellow, red, blue, green, brown, orange and violet.

A coloured UV curable inkjet ink contains preferably a colour pigment and a dispersant, more preferably a polymeric dispersant, for dispersing the colour pigment. The UV curable inkjet ink may also contain a dispersion synergist to improve the dispersion quality and stability of the ink. A mixture of dispersion synergists may be used to further improve dispersion stability.

The surface tension of the UV curable inkjet ink is preferably from 20 to 35 mN/m at 25° C., more preferably not more than 22 mN/m from the viewpoint of the wettability.

For having a good ejecting ability, the viscosity of the UV curable inkjet ink at the jetting temperature is preferably smaller than 30 mPa·s, more preferably smaller than 15 mPa·s, and most preferably between 4 and 13 mPa·s at a shear rate of 1000 s$^{-1}$ and a temperature of 45° C.

The UV curable composition or inkjet ink may further also contain at least one inhibitor for improving the thermal stability of the composition or inkjet ink.

The UV curable composition or inkjet ink may further also contain at least one surfactant for obtaining good spreading characteristics on a substrate.

In a preferred embodiment, the UV curable inkjet ink is part of a UV curable inkjet ink set. The UV curable inkjet ink set preferably includes at least a cyan UV curable inkjet ink, a magenta UV curable inkjet ink, a yellow UV curable inkjet ink and a black UV curable inkjet ink. The UV curable CMYK-inkjet ink set may also be extended with extra inks such as red, green, blue, and/or orange to further enlarge the colour gamut of the image. The UV curable inkjet ink set may also be extended by the combination of the full density inkjet inks with light density inkjet inks. The combination of dark and light colour inks and/or black and grey inks improves the image quality by a lowered graininess.

The UV curable ink set may also include one or more spot colours, preferably one or more corporate colours, such as e.g. the red colour of Coca-Cola™.

The UV curable inkjet ink set may also include a varnish. The UV curable inkjet ink set preferably also includes a white inkjet ink.

Other Photoinitiators and Co-Initiators

The UV curable composition or inkjet ink contains the mixture of photoinitiators according to Formula (I) and (II) in an amount of 2 to 20 wt %, more preferably 3 to 17 wt %, and most preferably 5 to 15 wt % wherein the weight percentage (wt %) is based on the total weight of the UV curable composition or inkjet ink.

Other photoinitiators may also be added to the UV curable composition or inkjet ink.

An acylphosphine oxide is preferably used in combination with the mixture of photoinitiators according to Formula (I) and (II). The acyl phosphine oxide is preferably a bisacylphosphine oxide.

In a preferred embodiment, the acylphosphine oxide is a polymerizable acylphosphine oxide, more preferably a polymerizable bisacylphosphine oxide.

For primary food packaging applications, the one or more other photoinitiators are preferably selected from the group consisting of polymerizable photoinitiators, polymeric photoinitiators and multifunctional photoinitiators. A multifunctional photoinitiator is a photoinitiator having two or more photoinitiating groups, e.g. two benzophenone groups and a thioxanthone group. In a more preferred embodiment, the one or more other photoinitiators are a polymerizable photoinitiator. Such a photoinitiator results in a smaller viscosity than a polymeric photoinitiator while still minimizing health risks in food packaging applications.

The other photoinitiators in the UV curable inkjet ink are preferably free radical initiators, more specifically a Norrish type I initiator or a Norrish type II initiator. A free radical photoinitiator is a chemical compound that initiates polymerization of monomers when exposed to actinic radiation by the formation of a free radical. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or a co-initiator. Both type I and type II photoinitiators can be used in the present invention, alone or in combination. The free radical UV curable inkjet ink preferably includes no cationic photoinitiator.

The polymerizable photoinitiators may be combined with other type of non-polymeric or non-polymerizable photoinitiators, for food packaging applications at concentration levels in the inkjet ink causing no health risks, e.g. due to migration into the foodstuff. Suitable photoinitiators are disclosed in CRIVELLO, J. V., et al. Photoinitiators for Free Radical Cationic and Anionic Photopolymerization. 2nd edition. Edited by BRADLEY, G. London, UK: John Wiley and Sons Ltd, 1998. p. 287-294.

For a low migration UV curable composition or inkjet ink, the photoinitiator preferably consists of so-called diffusion hindered photoinitiator. A diffusion hindered photoinitiator is a photoinitiator which exhibits a much lower mobility in a cured layer of the UV curable inkjet ink than a monofunctional photoinitiator, such as benzophenone. Several methods can be used to lower the mobility of the photoinitiator. One way is to increase the molecular weight of the photoinitiators so that the diffusion speed is reduced, e.g. polymeric photoinitiators. Another way is to increase its reactivity so that it is built into the polymerizing network, e.g. multifunctional photoinitiators (having 2, 3 or more photoinitiating groups) and polymerizable photoinitiators.

The diffusion hindered photoinitiator is preferably selected from the group consisting of non-polymeric multifunctional photoinitiators, oligomeric or polymeric photoinitiators and polymerizable photoinitiators. Non-polymeric di- or multifunctional photoinitiators are considered to have a molecular weight between 300 and 900 Dalton. Non-polymerizable monofunctional photoinitiators with a molecular weight in that range are not diffusion hindered photoinitiators.

Most preferably the photoinitiators in the UV curable inkjet ink consist of one or more diffusion hindered photoinitiators, preferably one or more polymerizable or polymeric photoinitiators, and more preferably polymerizable photoinitiators.

Preferred diffusion hindered photoinitiators contain one or more photoinitiating functional groups derived from a Norrish type I-photoinitiator selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones and phenylglyoxalates.

Preferred diffusion hindered photoinitiators contain one or more photoinitiating functional groups derived from a Norrish type II-initiator selected from the group consisting of benzophenones, 1,2-diketones and anthraquinones.

Suitable diffusion hindered photoinitiators are also those disclosed in EP 2065362 A (AGFA) and EP 2161264 A (AGFA).

In a photoinitiating system, one of the photoinitiators can also function as a sensitizer enhancing the reactivity of another photoinitiator. Preferred sensitizers are polymerizable sensitizers such as those disclosed in EP 2053095 A (FUJIFILM).

In order to increase the photosensitivity further, the free radical UV curable composition or inkjet ink may additionally contain no non-polymerizable, no non-polymeric co-initiators. Suitable examples of these co-initiators can be categorized in three groups: 1) tertiary aliphatic amines such as methyldiethanolamine, dimethylethanolamine, triethanolamine, triethylamine and N-methylmorpholine; (2) aromatic amines such as amylparadimethylaminobenzoate, 2-n-butoxyethyl-4-(dimethylamino) benzoate, 2-(dimethylamino)ethylbenzoate, ethyl-4-(dimethylamino) benzoate, and 2-ethylhexyl-4-(dimethylamino)benzoate; and (3) (meth)acrylated amines such as dialkylamino alkyl (meth)acrylates (e.g., diethylaminoethylacrylate) or N-morpholinoalkyl-(meth)acrylates (e.g., N-morpholinoethylacrylate). The preferred co-initiators are aminobenzoates.

When one or more of these co-initiators are included into the UV curable inkjet ink, for food packaging applications amounts are used causing no health risks, e.g. due to migration into the foodstuff.

The free radical UV curable composition or inkjet ink preferably includes the other co-initiator in an amount of 0.1 to 10.0 wt %, more preferably in an amount of 0.5 to 5.0 wt %, most preferably in an amount of 1.0 to 3.0 wt % of the total weight of the free radical UV curable composition or inkjet ink.

The UV curable composition or inkjet ink preferably does not include a photoinitiator selected from the group of 2-hydroxy 2-methyl propiophenone, benzophenone, 2-methyl benzophenone, 4-methyl benzophenone, 2,4,6-trimethylbenzo-phenone, 1-hydroxycyclohexyl phenylketone, 2,2-dimethoxy 2-phenyl acetophenone, 2-methyl 4'-(methylthio) 2-morpholinopropiophenone, 4-isopropyl 9H-thioxanthen-9-one, 2-isopropyl 9H-thioxanthen-9-one, and 2,4-diethyl 9H-thioxanthen-9-one. Such a UV curable composition has no doubtful toxicology.

Polymerization Inhibitors

The UV curable inkjet ink may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol may also be used.

Suitable commercial inhibitors are, for example, Sumilizer™ GA-80, Sumilizer™ GM and Sumilizer™ GS produced by Sumitomo Chemical Co. Ltd.; Genorad™ 16, Genorad™ 18 and Genorad™ 20 from Rahn AG; Irgastab™ UV10 and Irgastab™ UV22, Tinuvin™ 460 and CGS20 from Ciba Specialty Chemicals; Floorstab™ UV range (UV-1, UV-2, UV-5 and UV-8) from Kromachem Ltd, Additol™ S range (S100, S110, S120 and S130) from Cytec Surface Specialties.

A preferred polymerization inhibitor is Irgastab™ UV10 from BASF.

In a preferred embodiment, the polymerization inhibitor is a mixture of different types of polymerization inhibitors. Preferred polymerization inhibitors are mixtures of an oxyl free radical-based polymerization inhibitor, a phenol-based polymerization inhibitor, and an amine-based polymerization inhibitor. Suitable examples are given in EP 2851402 A (FUJIFILM).

Since excessive addition of these polymerization inhibitors will lower the ink sensitivity to curing, it is preferred that the amount capable of preventing polymerization is determined prior to blending. The amount of a polymerization inhibitor is preferably lower than 2 wt % based on the total weight of the UV curable inkjet ink.

A preferred polymerization inhibitor is butylhydroxytoluene for reasons of food safety.

Suitable polymerization inhibitors include phenol type antioxidants, hindered amine light stabilizers, phosphor type antioxidants, hydroquinonemonomethyl ether commonly used in (meth)acrylate monomers, and hydroquinone, t-butylcatechol, pyrogallol may also be used.

Suitable commercial inhibitors are, for example, Sumilizer™ GA-80, Sumilizer™ GM and Sumilizer™ GS produced by Sumitomo Chemical Co. Ltd.; Genorad™×16, Genorad™ 18 and Genorad™ 20 from Rahn AG; Irgastab™ UV10 and Irgastab™ UV22, Tinuvin™ 460 and CGS20 from BASF; Floorstab™ UV range (UV-1, UV-2, UV-5 and UV-8) from Kromachem Ltd, Additol™ S range (S100, 5110, 5120 and 5130) from Cytec Surface Specialties.

Since excessive addition of these polymerization inhibitors will lower the ink sensitivity to curing, the amount of a polymerization inhibitor is preferably less than 1 wt % of the UV curable composition or inkjet ink.

Polymerizable Compounds

The UV curable composition or inkjet ink may include one or more monomers and/or oligomers. Any monomer and oligomer capable of free radical polymerization may be used in the UV curable composition or inkjet ink. The monomers and oligomers may have different degrees of polymerizable functionality, and a mixture including combinations of mono-, di-, tri- and higher polymerizable functionality monomers may be used. The viscosity of the UV curable inkjet ink can be adjusted by varying the ratio between the monomers.

The monomers and oligomers used, especially for food packaging applications, are preferably purified compounds having no or almost no impurities, more particularly no toxic or carcinogenic impurities. The impurities are usually derivative compounds obtained during synthesis of the polymerizable compound. Purification methods are well-known to those skilled in the art of manufacturing monomers and oligomers. Sometimes, however, some compounds may be added deliberately to pure polymerizable compounds in harmless amounts, for example, polymerization inhibitors or stabilizers.

Particularly preferred monomers and oligomers are those listed in [0106] to [0115] in EP 1911814 A (AGFA).

In a preferred embodiment, the UV curable composition or inkjet ink includes at least one monomer selected from the group consisting of 3-methyl 1,5-pentanediol diacrylate, dipropyleneglycol diacrylate, ethoxylated trimethylolpropane triacrylate, pentaerythritol tetraacrylate, and cyclic trimethylolpropane formal acrylate.

For achieving high printing speeds, preferably low viscous monomers are used so that a low viscosity for the free radical UV curable inkjet ink can be obtained. However, in industrial inkjet printing also a high reliability is required which allows the incorporation of the inkjet printing system into a production line. In a preferred embodiment, the low viscous monomer loses less than 15% of its weight when kept at 40° C. for 100 hours in an open cubic vessel.

Colorants

The UV curable inkjet ink may contain a colorant. Colorants used in the curable inks may be dyes, pigments or a combination thereof. Organic and/or inorganic pigments may be used.

The colorant is preferably a pigment or a polymeric dye, most preferably a colour pigment. In food packaging applications, low molecular weight dyes, e.g. smaller than 1000 Dalton, can still migrate into the food or be extracted by the food giving undesired coloration of the food, or even worse allergic reactions after consuming the solid or liquid food.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley-VCH, 2004. ISBN 3527305769.

Particular preferred pigments are C.I. Pigment Yellow 1, 3, 10, 12, 13, 14, 17, 55, 65, 73, 74, 75, 83, 93, 97, 109, 111, 120, 128, 138, 139, 150, 151, 154, 155, 175, 180, 181, 185, 194 and 213.

Particular preferred pigments are C.I. Pigment Red 17, 22, 23, 41, 48:1, 48:2, 49:1, 49:2, 52:1, 57:1, 88, 112, 122, 144, 146, 149, 170, 175, 176, 184, 185, 188, 202, 206, 207, 210, 216, 221, 248, 251, 254, 255, 264, 266, 270 and 272.

Particular preferred pigments are C.I. Pigment Violet 19, 23, 32, and 37.

Particular preferred pigments are C.I. Pigment Blue 15:1, 15:2, 15:3, 15:4, 15:6, 16, 56, 61 and (bridged) aluminium phthalocyanine pigments.

Particular preferred pigments are C.I. Pigment Orange 5, 13, 16, 34, 40, 43, 59, 66, 67, 69, 71 and 73.

Particular preferred pigments are C.I. Pigment Green 7 and 36.

Particular preferred pigments are C.I. Pigment Brown 6 and 7.

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia™ Magenta RT-355-D from BASF AG.

Carbon black is preferred as a black pigment. Suitable black pigments include carbon blacks such as Pigment Black 7 (e.g. Carbon Black MA8® from MITSUBISHI CHEMICAL), Regal® 400R, Mogul® L, Elftex® 320 from CABOT Co., or Carbon Black FW18, Special Black 250, Special Black 350, Special Black 550, Printex® 25, Printex® 35, Printex® 55, Printex® 90, Printex® 150T from DEGUSSA. In a preferred embodiment, the carbon black pigment used is a pigment having less than 0.15% of toluene-extractable fraction using the method as described in section III, paragraph 5 of the Resolution AP(89) 1 dated 13 Sep. 1989 published by the Council of Europe.

It is also possible to make mixtures of pigments. For example, in some inkjet ink application a neutral black inkjet ink is preferred and can be obtained e.g. by mixing a black pigment and a cyan pigment into the ink. Also pigments may be combined to enlarge the colour gamut of an ink set. The inkjet application may also require one or more spot colours. Silver and gold are often desired colours for making a product more attractive by giving it an exclusive appearance.

Also non-organic pigments may be present in the inks. Suitable pigments are C.I. Pigment Metal 1, 2 and 3. Illustrative examples of the inorganic pigments include titanium oxide, barium sulphate, calcium carbonate, zinc oxide, lead sulphate, yellow lead, zinc yellow, red iron oxide (III), cadmium red, ultramarine blue, prussian blue, chromium oxide green, cobalt green, amber, titanium black and synthetic iron black. However, care should be taken to prevent migration and extraction of heavy metals in food application. In the preferred embodiment no pigments are used which contain a heavy metal selected from the group consisting of arsenic, lead, mercury and cadmium. In a more preferred embodiment, no inorganic pigments are used in the inkjet ink with the exception of titanium oxide, and calcium carbonate.

Pigment particles in inkjet ink should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 µm, more preferably between 0.070 and 0.300 µm and particularly preferably between 0.080 and 0.200 µm. Most preferably, the numeric average pigment particle size is no larger than 0.150 µm. An average particle size smaller than 0.050 µm is less desirable for decreased light-fastness, but mainly also because very small pigment particles or individual pigment molecules thereof may still be extracted in food packaging applications.

The numeric average pigment particle size of pigment particles is best determined with a Brookhaven Instruments Particle Sizer BI90plus based upon the principle of dynamic light scattering. The ink is then diluted, for example, with ethyl acetate to a pigment concentration of 0.002 wt %. The measurement settings of the BI90plus are: 5 runs at 23° C., angle of 90°, wavelength of 635 nm and graphics=correction function.

In the case of a white UV curable ink, preferably a pigment with a refractive index greater than 1.60, preferably greater than 2.00, more preferably greater than 2.50 and most preferably greater than 2.60 is used. The white pigments may be employed singly or in combination.

Preferably titanium dioxide is used for the pigment with a refractive index greater than 1.60. Titanium oxide occurs in the crystalline forms of anatase type, rutile type and brookite type. The anatase type has a relatively low density and is easily ground into fine particles, while the rutile type has a relatively high refractive index, exhibiting a high covering power. Either one of these is usable in this invention. It is preferred to make the most possible use of characteristics and to make selections according to the use thereof. The use of the anatase type having a low density and a small particle size can achieve superior dispersion stability, ink storage stability and ejectability. At least two different crystalline forms may be used in combination. The combined use of the anatase type and the rutile type which exhibits a high colouring power can reduce the total amount of titanium oxide, leading to improved storage stability and ejection performance of ink.

For surface treatment of the titanium oxide, an aqueous treatment or a gas phase treatment is applied, and an alumina-silica treating agent is usually employed. Untreated-, alumina treated- or alumina-silica treated-titanium oxide are employable.

The numeric average particle diameter of the titanium oxide or other white pigments is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a Malvern™ nano-S available from Goffin-Meyvis. A sample can, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Generally pigments are stabilized in the dispersion medium by dispersing agents, such as polymeric dispersants or surfactants. However, the surface of the pigments can be modified to obtain so-called "self-dispersible" or "self-dispersing" pigments, i.e. pigments that are dispersible in the dispersion medium without dispersants.

The pigment is preferably used in a pigment dispersion used for preparing inkjet inks in an amount of 10 to 40 wt %, more preferably of 15 to 30 wt % based on the total weight of the pigment dispersion. In a curable inkjet ink the pigment is preferably present in an amount of 0.1 to 20 wt %, preferably 1 to 10 wt % based on the total weight of the inkjet ink.

Polymeric Dispersants

Typical polymeric dispersants are copolymers of two monomers but may contain three, four, five or even more monomers. The properties of polymeric dispersants depend on both the nature of the monomers and their distribution in the polymer. Copolymeric dispersants preferably have the following polymer compositions:
  statistically polymerized monomers (e.g. monomers A and B polymerized into ABBAABAB);
  alternating polymerized monomers (e.g. monomers A and B polymerized into ABABABAB);
  gradient (tapered) polymerized monomers (e.g. monomers A and B polymerized into AAABAABBABBB);
  block copolymers (e.g. monomers A and B polymerized into AAAAABBBBBB) wherein the block length of each of the blocks (2, 3, 4, 5 or even more) is important for the dispersion capability of the polymeric dispersant;
  graft copolymers (graft copolymers consist of a polymeric backbone with polymeric side chains attached to the backbone); and
  mixed forms of these polymers, e.g. blocky gradient copolymers.

Suitable polymeric dispersants are listed in the section on "Dispersants", more specifically [0064] to [0070] and to [0077], in EP 1911814 A (AGFA GRAPHICS) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100,000, more preferably smaller than 50,000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:
  DISPERBYK™ dispersants available from BYK CHEMIE GMBH;
  SOLSPERSE™ dispersants available from LUBRIZOL;
  TEGO™ DISPERS™ dispersants from EVONIK;
  EDAPLAN™ dispersants from MUNZING CHEMIE;

ETHACRYL™ dispersants from LYONDELL;
GANEX™ dispersants from ISP;
DISPEX™ and EFKA™ dispersants from BASF;
DISPONER™ dispersants from DEUCHEM.

Particularly preferred polymeric dispersants include Solsperse™ dispersants from LUBRIZOL, Efka™ dispersants from BASF and Disperbyk™ dispersants from BYK CHEMIE GMBH. Particularly preferred dispersants are Solsperse™ 32000, 35000 and 39000 dispersants from LUBRIZOL.

The polymeric dispersant is preferably used in an amount of 2 to 600 wt %, more preferably 5 to 200 wt %, most preferably 50 to 90 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The dispersion synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include Solsperse™ 5000 and Solsperse™ 22000 from LUBRIZOL.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. Solsperse™ 5000 from LUBRIZOL is preferred. Suitable dispersion synergists for yellow inkjet inks include those disclosed in EP 1790697 A (AGFA GRAPHICS).

Surfactants

The UV curable composition or inkjet ink may contain at least one surfactant. The surfactant can be anionic, cationic, non-ionic, or zwitter-ionic and is preferably added in a total quantity less than 3 wt % based on the total weight of the ink and particularly in a total less than 1 wt % based on the total weight of the free radical curable inkjet ink.

Preferred surfactants are selected from fluoro surfactants (such as fluorinated hydrocarbons) and silicone surfactants. The silicone surfactants are preferably siloxanes and can be alkoxylated, polyester modified, polyether modified, polyether modified hydroxy functional, amine modified, epoxy modified and other modifications or combinations thereof. Preferred siloxanes are polymeric, for example polydimethylsiloxanes.

Preferred commercial silicone surfactants include BYK™ 333 and BYK™ UV3510 from BYK Chemie.

In a preferred embodiment, the surfactant is a polymerizable compound.

Preferred polymerizable silicone surfactants include a (meth)acrylated silicone surfactant. Most preferably the (meth)acrylated silicone surfactant is an acrylated silicone surfactant, because acrylates are more reactive than methacrylates.

In a preferred embodiment, the (meth)acrylated silicone surfactant is a polyether modified (meth)acrylated polydimethylsiloxane or a polyester modified (meth)acrylated polydimethylsiloxane.

Preferred commercially available (meth)acrylated silicone surfactants include: Ebecryl™ 350, a silicone diacrylate from Cytec; the polyether modified acrylated polydimethylsiloxane BYK™ UV3500 and BYK™ UV3530, the polyester modified acrylated polydimethylsiloxane BYK™ UV3570, all manufactured by BYK Chemie; Tego™ Rad 2100, Tego™ Rad 2200N, Tego™ Rad 2250N, Tego™ Rad 2300, Tego™ Rad 2500, Tego™ Rad 2600, and Tego™ Rad 2700, Tego™ RC711 from EVONIK; Silaplane™ FM7711, Silaplane™ FM7721, Silaplane™ FM7731, Silaplane™ FM0711, Silaplane™ FM0721, Silaplane™ FM0725, Silaplane™ TM0701, Silaplane™ TM0701T all manufactured by CHISSO Corporation; and DMS-R05, DMS-R11, DMS-R18, DMS-R22, DMS-R31, DMS-U21, DBE-U22, SIB1400, RMS-044, RMS-033, RMS-083, UMS-182, UMS-992, UCS-052, RTT-1011 and UTT-1012 all manufactured by GELEST Inc.

Preparation of UV Curable Inkjet Inks

The preparation of pigmented UV curable inkjet inks is well-known to the skilled person. Preferred methods of preparation are disclosed in paragraphs [0076] to [0085] of WO 2011/069943 (AGFA).

Printing Devices

Preferred printing devices are inkjet printing devices. The UV curable inkjet ink is jetted by one or more print heads ejecting small droplets in a controlled manner through nozzles onto a substrate moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with inkjet ink or liquid. When the voltage is again removed, the ceramic expands to its original shape, ejecting a drop of ink from the print head.

A preferred piezoelectric print head is a so called push mode type piezoelectric print head, which has a rather large piezo-element capable of ejecting also high viscous inkjet ink droplets. Such a print head is available from RICOH as the GEN5s print head.

A preferred piezoelectric print head is a so-called through-flow piezoelectric drop-on-demand print head. Such a print head is available from TOSHIBA TEC as the CF1ou print head.

The inkjet print head normally scans back and forth in a transversal direction across the moving ink-receiver surface. Often the inkjet print head does not print on the way back. Bi-directional printing is preferred for obtaining a high areal throughput.

Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

In a particularly preferred embodiment, the inkjet printing of the UV curable inkjet ink is performed in a multi-pass printing mode. Multi-pass printing is a technique used to reduce banding in ink-jet printing. Dots of ink, when still in liquid form, tend to run together due to surface tension. This is referred to as coalescence. To print a high quality image it is important to print individual round dots. But to achieve full saturated colours, the dots must overlap to completely cover the paper. By only printing a portion of the image data so as to avoid simultaneously printing adjacent dots during each printing cycle, coalescence may be largely avoided. Additionally, by avoiding all horizontal adjacencies, the transverse speed of the printing mechanism can be increased up to two times the rated print speed of the print head. In a preferred embodiment, the number of passes used is to 2 to 6 passes, more preferably no more than 4 passes.

An advantage of using a multi-pass printing mode is that the UV curable inkjet ink is cured in a consecutive passes, rather than in a single pass which would require a curing device with a high UV output. The print head lifetime is also larger for multi pass printing. While in single pass printing one side shooter is sufficient to replace the whole print head, in multi pass printing side shooters and even failings can be tolerated. Also the cost of a multi-pass printer is usually much lower, especially for wide format substrates.

Curing Devices

The UV curable inkjet ink according to the present invention is cured by ultraviolet radiation.

In inkjet printing, the UV curing device may be arranged in combination with the print head of the inkjet printer, travelling therewith so that the UV curable inkjet ink is exposed to curing radiation very shortly after been jetted.

In such an arrangement it can be difficult to provide a small enough UV radiation source connected to and travelling with the print head. Therefore, a static fixed radiation source may be employed, e.g. a source of curing UV-light, connected to the radiation source by means of flexible radiation conductive means such as a fibre optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:

UV-A: 400 nm to 320 nm
UV-B: 320 nm to 290 nm
UV-C: 290 nm to 100 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

In a particularly preferred embodiment, the UV curing is performed using UV LEDs having an emission wavelength higher than 370 nm.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

INDUSTRIAL APPLICABILITY

The UV curable compositions and inkjet inks can be advantageously used for printing of food and pharmaceutical packaging.

There is no real limitation on the type of substrate for printing. The substrates are preferably substantially non-absorbing substrates such as e.g. a substrate having a polyethyleneterephthalate surface.

Preferred substrates include surfaces or consist of polyethylene, polypropylene, polycarbonate, polyvinyl chloride, polyesters like polyethylene terephthalate (PET), polyethylene naphthalate (PEN) and polylactide (PLA), polyethyleenfuranoate (PEF) and polyimide.

EXAMPLES

Materials

All compounds and solvents were readily available from fine chemical suppliers such as ACROS or ALDRICH unless otherwise specified. The water used was demineralized water.

VEEA is 2-(2-vinyloxyethoxy)ethyl acrylate available from Nippon Shokubai, Japan.

Catalyst Type A is a pyridine sulfonic acid catalyst available from SYNTHON Chemicals GmbH & Co, which was mortared to reduce the particle size.

Catalyst Type B is a pyridine sulfonic acid catalyst available from ACROS.

BHT is butylhydroxytoluene.

Acetonitrile was supplied by FLUKA.

Omnipol™ TX is the di-ester of carboxymethoxy-thioxanthone and polytetramethyleneglycol 250, average MW of 790 and available from IGM Resins, Waalwijk, NL.

AG0, corresponding the photoinitiator according to Formula (III), was prepared according to the following procedure:

395 g Omnipol™ TX was dissolved in 1850 ml dimethyl sulfoxide. The reaction mixture was heated to 60° C. and 363 g (3 mol) tris(hydroxymethyl) amino methane and 415 g (3 mol) potassium carbonate were added. The reaction was allowed to continue for 2 hours at 60° C. The reaction mixture was allowed to cool down to room temperature. The precipitated salts were removed by filtration and the reaction mixture was added to a mixture of 1500 ml water and 250 ml acetone. The thioxanthone precipitated from the medium, was isolated by filtration and dried. The crude thioxanthone was treated with 1500 ml acetone, isolated by filtration and dried. 260 g of AG0 was isolated (TLC-analysis: RP-C18 (Partisil KC18F, supplied by Whatman), eluent MeOH/0.5 M NaCl 85/15, $R_f$=0.71).

DB162 is an abbreviation used for the polymeric dispersant Disperbyk™ 162 available from BYK CHEMIE GMBH whereof the solvent mixture of 2-methoxy-1-methylethylacetate, xylene and n-butylacetate was removed. The polymeric dispersant is a polyester-polyurethane dispersant on the basis of caprolacton and toluene diisocyanate having an amine value of 13 mg KOH/g, a Mn of about 4,425 and a Mw of about 6,270.

Sun Fast™ Blue 15:4 is a C.I. Pigment Blue 15:4 pigment from SUN CHEMICAL.

INHIB is a mixture forming a polymerization inhibitor having a composition according to Table 2.

TABLE 2

| wt % of Component | INHIB |
|---|---|
| VEEA | 82.4 |
| p-methoxyphenol | 4.0 |
| 2,6-di-tert-butyl-4-methylphenol | 10.0 |
| Cupferron ™ AL | 3.6 |

Cupferron™ AL is aluminum N-nitrosophenylhydroxylamine from WAKO CHEMICALS LTD.

PETRA is pentaerythritol tetraacrylate, a tetrafunctional monomer available as Sartomer™ SR295 from ARKEMA.

STAB UV10 is 4-hydroxy-2,2,6,6-tetramethylpiperidinooxy sebacate available as Irgastab™ UV 10 from BASF.

Genopol™ AB-2 is a polymeric aminobenzoate available from RAHN.

IC819 is a bis(2,4,6-trimethylbenzoyl)-phenylphosphineoxide photoinitiator available as Irgacure™ 819 from BASF.

BYK™ 333 is a polyether modified polydimethylsiloxane from BYK Chemie GmbH.

Tegorad™ 2100 is a radically cross-linkable silicone acrylate available from EVONIK. US 2011086221 (3M) describes Tegorad™ 2100 as:

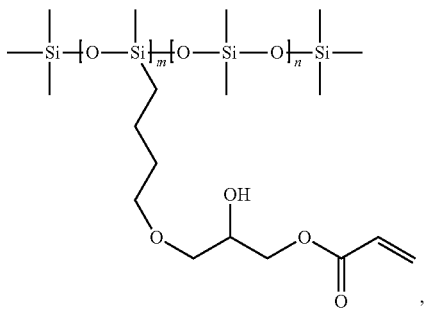

wherein n ranges from 10 to 20 and m ranges from 0.5 to 5.

PET100 is a 100 µm unsubbed PET substrate with on the backside an anti-blocking layer with antistatic properties available from AGFA-GEVAERT as P100C PLAIN/ABAS.

Measurement Methods

1. Average Particle Size Catalyst

The average particle size was measured using a Coulter™ LS13320 Tornado equipped with a dry powder module. The average particle size measured by laser diffraction is a volume weighted mean diameter (arithmetic mean size in volume % mode).

2. Specific Surface Area

The specific surface area of the solid catalyst particles was determined by a BET surface analysis using Tristar™ 3000 from MICROMERITICS using nitrogen gas as the adsorbate. The solid catalyst particles were first degassed for 24 hours at 25° C. on a Vacprep from MICROMERITICS.

3. HPLC

15 µl of each sample was injected on a HPLC using a Waters 2695 Separations module and a Waters 996 Photodiode Array Detector (254 nm). As a stationary phase is used first an Alltima™ C15-5 µm Guard column (7.5×3.0 mm) and then an Alltima™ C18-5 µm column (150×3.2 mm), both supplied by ALLTECH. A flow rate of 0.8 ml/min was used at a temperature of 30° C. The gradient with acetonitrile/water 10/90+0.02M NH$_4$OAc as Eluent A and acetonitrile as Eluent B used for the determination of the thioxanthones is given in Table 3.

TABLE 3

| Time | % eluent A | % eluent B |
|---|---|---|
| 0 min | 80 | 20 |
| 12 min | 0 | 100 |
| 14 min | 0 | 100 |
| 14 min + 10 sec | 80 | 20 |
| 20 | 80 | 20 |
| 20 min + 10 sec | Stop flow | |

The amount of the different photoinitiators was determined by area %. Using a calibration, the area % obtained by the HPLC was calculated into a wt % based on the total weight of the photoinitiators.

4. Curing Speed

A UV curable inkjet ink was coated on a PET100 substrate, using a bar coater and a 10 μm wired bar. The coated sample was mounted on a belt, transporting the sample under a Phoseon™ Fire Line 125 LED curing device with an output wavelength of 395 nm, at a speed of 30 m/min using 4 W output at a distance of 4.5 mm from the LED. The curing speed was evaluated based on visual damage when using a Q-tip. The number of passes under the UV LED needed to obtain a cured image was registered.

5. Average Particle Size Pigment Dispersion

The particle size of pigment particles in a pigment dispersion was determined by photon correlation spectroscopy at a wavelength of 633 nm with a 4 mW HeNe laser on a diluted sample of the pigment dispersion. The particle size analyzer used was a Malvern™ nano-S available from Goffin-Meyvis.

6. Viscosity

The viscosity was measured at 45° C. and at a shear rate of 1,000 s$^{-1}$ using a Rotovisco™ RV1 viscometer from HAAKE.

7. Surface Tension

The static surface tension of a UV curable inkjet ink was measured with a KRÜSS tensiometer K9 from KRÜSS GmbH, Germany at 25° C. after 60 seconds.

Example 1

This example illustrates the synthesis by flow chemistry of the mixture of photoinitiators containing the polymerizable photoinitiators according to Formula (I) and (II).

Experiments and Results

A periodic flow chemistry apparatus was set up as shown by FIG. 1. The pulsating in-line pump (3) was combination of a peristaltic pump Shenchen™ N6-6L with DZ25-6L pump head and a pulsator modified Prominent™ beta/4 type (modification=removal of check valves) using a peristaltic hose Marprene type: 902.0048.024 #15 from Watson-Marlow. A flow rate of about 5 L/hour was used. The channel (4) was a polytetrafluoro ethylene (PTFE) tubing available from Bohlender GmbH having an internal diameter of 4 mm and a wall thickness of 0.5 mm. The part of the channel submerged in the oil bath was wound up as a circular helical tube having a radius of 6 to 9 cm. The pulsation frequency was 1.7 Hz.

A reaction mixture RM-1 was made having a composition as shown in Table 4. The weight percentages (wt %) are based on the total weight of the reaction mixture.

TABLE 4

| wt % of Component | RM-1 |
|---|---|
| AG0 | 20.30 |
| VEEA | 78.64 |
| BHT | 0.23 |
| Solid Catalyst Particles | 0.83 |

The same reaction mixture RM-1 was used in 11 different experiments wherein the reaction parameters and the type of solid catalyst particles were altered. The different experiments and results are shown in Table 5. The table should be read as follows for flow chemistry synthesis experiment N°1: Catalyst Type A was used as solid catalyst particles in the reaction mixture RM-1 and the reaction mixture in the channel (4) was heated in the oil bath (5) at 120° C. for 6 minutes. The resulting end product was analyzed using HPLC to determine the wt % of the different types of photoinitiators present. The notation AGx is used to identify the photoinitiators by the number x of acrylate groups present in their structure. So for example AG0 corresponds with the starting product, i.e. the photoinitiator according to Formula (III), while AG3 and AG4 correspond to the polymerizable photoinitiators of Formula (I) respectively Formula (II). The wt % is based on the total weight of all photoinitiators present.

TABLE 5

| | | Heating conditions | | wt % of photoinitiator AGx (x = number of acrylate groups) | | | | |
|---|---|---|---|---|---|---|---|---|
| N° | Catalyst | ° C. | minutes | AG0 | AG1 | AG2 | AG3 | AG4 |
| 1 | Type A | 120 | 6 | — | — | 5 | 87 | 8 |
| 2 | Type A | 120 | 6.5 | — | — | 5 | 86 | 9 |
| 3 | Type A | 120 | 7.5 | — | — | 4 | 86 | 10 |
| 4 | Type A | 120 | 9 | — | — | 3 | 87 | 10 |
| 5 | Type B | 120 | 7 | 76 | 7 | 13 | 4 | 2 |
| 6 | Type B | 120 | 9 | 60 | 11 | 20 | 9 | 2 |
| 7 | Type B | 120 | 11 | 47 | 13 | 22 | 16 | 2 |
| 8 | Type B | 130 | 10 | — | — | 16 | 79 | 5 |
| 9 | Type B | 130 | 11 | — | — | 5 | 88 | 7 |
| 10 | Type B | 130 | 12 | — | — | 2 | 89 | 9 |
| 11 | Type B | 130 | 13 | — | — | — | 91 | 9 |

From Table 5, it is immediately apparent that the selection of reaction conditions is straight forward in order to obtain the photoinitiator mixture in accordance with the invention. The catalyst A has an average particle size of 12 μm and due to its large specific surface area (0.49 m$^2$/g), the reaction was completed in 6 to 9 minutes at 120° C. (see experiments N° 1 to 4). The same reaction conditions are insufficient for full conversion of the photoinitiator AG0 when using catalyst Type B having a larger average particle size of 336 μm and a small specific surface area (<0.03 m$^2$/g), as shown by the experiments N° 5 to 7. Using a heating temperature of 130° C. instead of 120° C. in the experiments N° 8 to 11 allows for full conversion of AG0.

A duration experiment was conducted for 5 hours with the reaction conditions of N° 3. Samples were taken every half hour and compared. The composition of the end product as mentioned in Table 5 remained almost constant. No clogging was observed. A similar experiment was set up wherein the oscillation motion was omitted, i.e. no periodic flow. This resulted in clogging of the channel after only 1.5 hours.

Another duration experiment was conducted for 8 hours with the reaction conditions of N°10. Again neither noticeable changes in the composition of the final photoinitiator mixture, nor any clogging of the channel could be observed.

Example 2

This example illustrates the advantages of the mixture of photoinitiators when used in UV curable inkjet inks.

Batch Synthesis of the PI-Batch 17.12 g of AG0 was added to a mixture of 40.92 g VEEA and 25.35 g isopropyl acetate. 700 mg 3-pyridine sulfonic acid was added and the mixture was heated to 85° C. for 7 hours. TLC-analysis indicated complete conversion of AG0 ((TLC on Partisil KC18F, supplied by Whatman, eluent MeOH/0.5 M NaCl 85/15, R$_f$: 0.3). The reaction mixture was allowed to cool down to room temperature and the catalyst was removed by filtration. The isopropyl acetate was removed under reduced pressure. The polymerizable photoinitiator is referenced here below to as Batch-PI.

Cyan Pigment Dispersion C-DISP

A 30 wt % solution of DB162 in VEEA was prepared. 1 wt % INHIB was added. 1.5 kg Sun Fast™ Blue 15:4 was added to a mixture of 1.95 kg VEEA, 2.5 kg of the DB162 solution and 50 g INHIB while stirring with a DISPER-LUX™ dispenser. Stirring was continued for 30 minutes. The vessel was connected to a DYNO™-MILL ECM Poly mill from the company Willy A. Bachofen (Switzerland), preloaded with 1.5 kg 2-(2"-vinyloxyethoxy)ethyl acrylate and filled for 42% with 0.4 mm yttrium stabilized zirconia beads ("high wear resistant zirconia grinding media" from TOSOH Co.). The mixture was circulated over the mill for 5 hours 52 minutes at a flow rate of 1.5 l/min and a rotation speed in the mill of about 13 m/s. During the milling procedure, an additional 2.5 kg of the DB162 solution was added. During the complete milling procedure the content in the mill was cooled to keep the temperature below 40° C. After milling, dispersion 1 was discharged into a 15 L-vessel. The resulting concentrated pigment dispersion C-DISP according to Table 6 exhibited an average particle size of 88 nm.

TABLE 6

| Component | wt % |
| --- | --- |
| Sun Fast ™ Blue 15:4 | 15.0 |
| DB162 | 15.0 |
| INHIB | 1.0 |
| VEEA | 69.0 |

Preparation of UV Curable Inkjet Ink

The UV curable inkjet inks COMP-1 and INV-1 were prepared by mixing the components for each UV curable inkjet ink according to Table 7 using the above prepared pigment dispersion DISP-C. The photoinitiator mixture of experiment N°10 was used and referenced by as PI-Flow in Table 7.

TABLE 7

| wt % of component | COMP-1 | INV-1 |
| --- | --- | --- |
| C-DISP | 22.43 | 22.43 |
| VEEA | 34.57 | 34.57 |
| PETRA | 4.00 | 4.00 |
| INHIB | 0.77 | 0.77 |
| PI-Batch | 25.00 | — |
| PI-Flow | — | 25.00 |
| STAB UV10 | 0.20 | 0.20 |
| Genopol ™ AB-2 | 5.00 | 5.00 |
| IC819 | 3.00 | 3.00 |
| BYK ™ 333 | 0.03 | 0.03 |
| Tegorad ™ 2100 | 5.00 | 5.00 |

Evaluation and Results

First, the thermal stability of the photoinitiator mixes PI-Batch and PI-Flow was determined by measuring the viscosity before and after storage at 60° C. The results are shown in Table 8.

TABLE 8

| Photoinitiator mixture | Viscosity (mPa · s) | | |
| --- | --- | --- | --- |
| | Fresh | After 7 days at 60° C. | After 14 days at 60° C. |
| PI-Batch | 19.5 | 31.0 | 45.6 |
| PI-Flow | 20.8 | 22.2 | 24.4 |

From Table 8, it is immediately clear that the thermal stability of the photoinitiator mixture made by a periodic flow synthesis is much better than that of the photoinitiator mixture made by batch synthesis.

Next the thermal stability of the UV curable inkjet inks COMP-1 and INV-1 was evaluated. The results are shown in Table 9.

TABLE 9

| Inkjet Ink | Viscosity (mPa · s) | | Surface Tension (mN/m) |
| --- | --- | --- | --- |
| | Fresh | After 7 days at 80° C. | |
| COMP-1 | 11.1 | 9% increase | 22.3 |
| INV-1 | 11.3 | 6% increase | 21.6 |

It can be seen that also that the UV curable inkjet INV-1 containing the photoinitiator mixture prepared by periodic flow chemistry is more stable then the UV curable inkjet COMP-1. Fluctuations in viscosity have a large impact on the jetting performance and reliability of print heads operating with low viscous inkjet inks.

The curing speed of the UV curable inkjet inks COMP-1 and INV-1 was determined. Both inkjet inks required three passes for full curing.

REFERENCE SIGNS LIST

TABLE 10

| 1 | Supply vessel |
| --- | --- |
| 2 | Stirrer |
| 3 | Pulsating in-line pump |
| 4 | Channel |
| 5 | Oil bath |
| 6 | Cooling bath |
| 7 | Product vessel |
| 8 | Curvatures of channel |

The invention claimed is:

1. A mixture of photoinitiators comprising:
a polymerizable photoinitiator according to Formula (I):

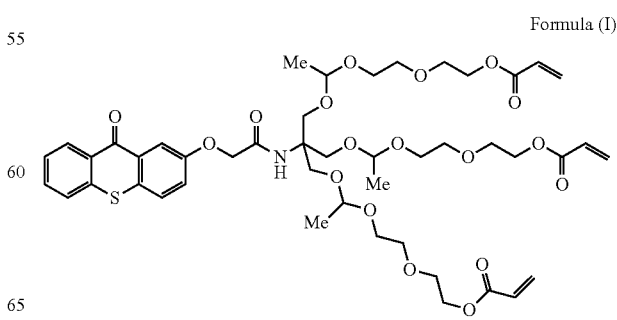

Formula (I)

and
a polymerizable photoinitiator according to Formula (II):

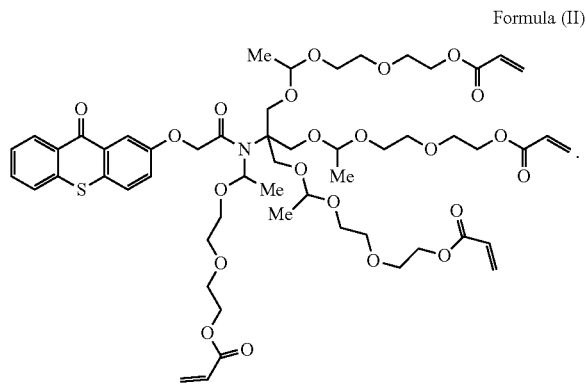 [SMILES: C=CC(=O)OCCOCCOC(C)OCC(COC(C)OCCOCCOC(=O)C=C)(COC(C)OCCOCCOC(=O)C=C)N(C(=O)COc1ccc2sc3ccccc3c(=O)c2c1)C(C)OCCOCCOC(=O)C=C]

Formula (II)

2. The mixture of photoinitiators according to claim 1, wherein the polymerizable photoinitiator according to Formula (I) is present in an amount of at least 75 wt % and the polymerizable photoinitiator according to Formula (II) is present in an amount of 0.1 wt % to 20.0 wt %, each based on a total weight of the polymerizable photoinitiators according to Formula (I) and (II).

3. The mixture of photoinitiators according to claim 1, wherein the mixture of photoinitiators consists of the polymerizable photoinitiator according to Formula (I) and the polymerizable photoinitiator according to Formula (II).

4. A UV curable composition comprising:
the mixture of photoinitiators according to claim 1; and
2-(2'-vinyloxyethoxy) ethylacrylate.

5. The UV curable composition according to claim 4, further comprising a colorant.

6. The UV curable composition according to claim 4, wherein the UV curable composition is a UV curable inkjet ink.

7. A method of manufacturing a mixture of photoinitiators, the method comprising the steps of:
flowing a reaction mixture including a photoinitiator according to Formula (III), solid catalyst particles having an average particle size between 10 µm and 500 µm, and 2-(2'-vinyloxyethoxy) ethylacrylate through a channel in a periodic flow at frequencies up to 100 Hz;

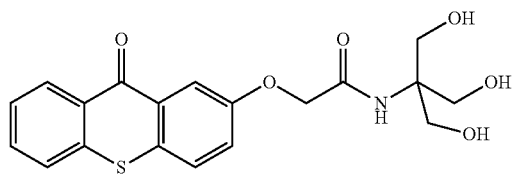

Formula (III)

heating the reaction mixture to a temperature above 90° C. so that a polymerizable photoinitiator according to Formula (II) is formed

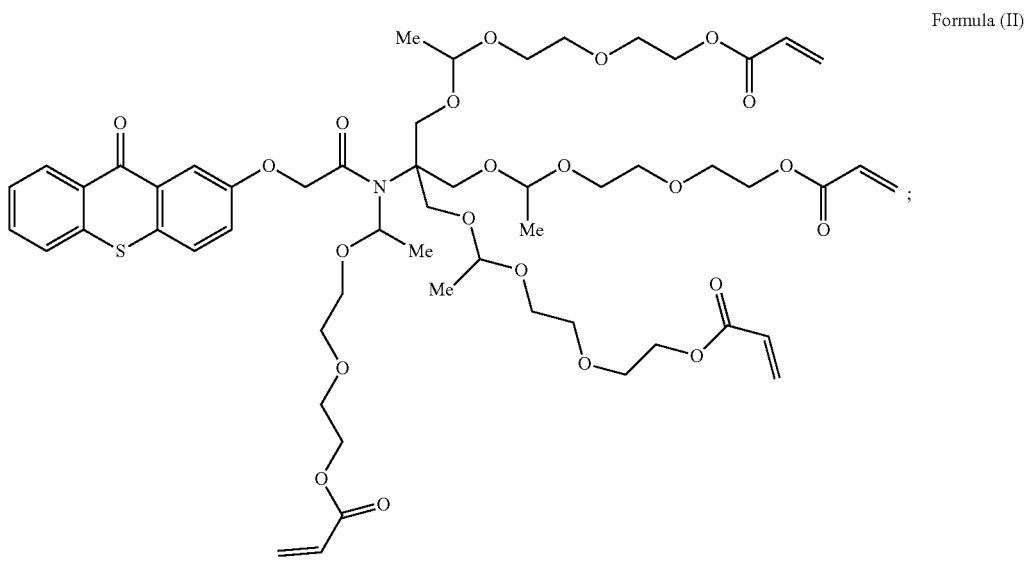 [SMILES: C=CC(=O)OCCOCCOC(C)OCC(COC(C)OCCOCCOC(=O)C=C)(COC(C)OCCOCCOC(=O)C=C)N(C(=O)COc1ccc2sc3ccccc3c(=O)c2c1)C(C)OCCOCCOC(=O)C=C]

Formula (II)

cooling the reaction mixture to a temperature below 30° C.; and removing the solid catalyst particles; wherein the average particle size is a volume weighted mean diameter measured by laser diffraction.

8. The method of manufacturing according to claim 7, wherein the solid catalyst particles consist essentially of pyridine-sulfonic acid.

9. The method of manufacturing according to claim 7, wherein no organic solvent is present in the reaction mixture.

10. The method of manufacturing according to claim 7, wherein the step of heating the reaction mixture includes:

heating the reaction mixture to a temperature between 100° C. and 150° C. for less than 20 minutes.

11. The method of manufacturing according to claim 7, wherein the periodic flow is created by a pulsating in-line pump.

12. The method of manufacturing according to claim 7, wherein the channel includes multiple curvatures.

13. The method of manufacturing according to claim 7, wherein the periodic flow is performed at a frequency between 2 Hz and 5 Hz.

14. An inkjet printing method comprising the steps of:

jetting onto a substrate a UV curable composition including the mixture of photoinitiators according to claim 1; and UV curing the UV curable composition using one or more UV LEDs at an emission wavelength higher than 360 nm.

15. The inkjet printing method according to claim 14, wherein the UV curable composition is a UV curable inkjet ink.

* * * * *